United States Patent
Rethy et al.

(10) Patent No.: US 7,479,150 B2
(45) Date of Patent: Jan. 20, 2009

(54) TROCAR INSERTION APPARATUS

(75) Inventors: Csaba Rethy, Fairfield, CT (US); Thomas Wanchell, Durham, CT (US); Kourosh Azarbarzin, Fairfield, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 705 days.

(21) Appl. No.: 10/943,132

(22) Filed: Sep. 16, 2004

(65) Prior Publication Data

US 2005/0203565 A1 Sep. 15, 2005

Related U.S. Application Data (60) Provisional application No. 60/504,506, filed on Sep. 19, 2003.

(51) Int. Cl.
*A61M 29/00* (2006.01)

(52) U.S. Cl. .................................... 606/198; 600/184

(58) Field of Classification Search ................. 600/184; 606/198

See application file for complete search history.

(56) References Cited

U.S. PATENT DOCUMENTS

| 219,296 A | 9/1879 | Naylor, Jr. |
| 319,296 A | 6/1885 | Molesworth |
| 668,879 A | 2/1901 | Miller |
| 702,789 A | 6/1902 | Gibson |
| 1,213,001 A | 1/1917 | Philips |
| 1,248,492 A | 12/1917 | Hill |
| 2,548,602 A | 4/1951 | Greenburg |
| 2,566,499 A | 9/1951 | Richter |
| 3,509,883 A | 5/1970 | Dibelius |
| 3,545,443 A | 12/1970 | Ansari |
| 3,742,958 A | 7/1973 | Rundles |
| 3,788,318 A | 1/1974 | Kim et al. |
| 3,789,852 A | 2/1974 | Kim et al. |
| 3,811,449 A | 5/1974 | Gravlee et al. |
| 3,902,492 A | 9/1975 | Greenhalgh |
| 3,968,800 A | 7/1976 | Vilasi |

(Continued)

FOREIGN PATENT DOCUMENTS

EP 0177177 4/1986

(Continued)

OTHER PUBLICATIONS

Product brochure Bluntport, Auto Suture Company, a Division of U.S. Surgical Corp. (1992) 2 pgs.

(Continued)

*Primary Examiner*—Kevin T Truong
*Assistant Examiner*—Erin Colello (57) ABSTRACT

Apparatus for forming and enlarging a percutaneous penetration are disclosed. The apparatus includes an elongate dilation member including a radially expandable member having a first cross-sectional area; and an elongate expansion member including a tubular element having a second cross-sectional area which is larger than the first cross-sectional area. The apparatus further includes an advancing apparatus having a first arm with a first engaging feature for engaging the handle of the dilation member; a second arm with a second engaging feature for engaging the handle of the expansion member; and an operation member; the first arm and the second arm being connected so that operation of the operation member approximates the first engaging feature and the second engaging feature together.

22 Claims, 7 Drawing Sheets

U.S. PATENT DOCUMENTS

| | | | |
|---|---|---|---|
| 4,018,230 A | 4/1977 | Ochiai et al. | |
| 4,141,364 A | 2/1979 | Schultze | |
| 4,183,102 A | 1/1980 | Guiset | |
| 4,320,762 A | 3/1982 | Bentov | |
| 4,411,655 A | 10/1983 | Schreck | |
| 4,447,237 A | 5/1984 | Frisch et al. | |
| 4,461,281 A | 7/1984 | Carson | |
| 4,479,497 A | 10/1984 | Fogarty et al. | |
| 4,493,701 A | 1/1985 | Bootman et al. | |
| 4,504,268 A | 3/1985 | Herlitze | |
| 4,581,025 A | 4/1986 | Timmermans | |
| 4,589,868 A | 5/1986 | Dretler | |
| 4,601,710 A * | 7/1986 | Moll | 604/164.12 |
| 4,601,713 A | 7/1986 | Fuqua | |
| 4,610,688 A | 9/1986 | Silvestrini et al. | |
| 4,630,609 A | 12/1986 | Chin | |
| 4,650,466 A | 3/1987 | Luther | |
| 4,654,030 A * | 3/1987 | Moll et al. | 604/164.12 |
| 4,706,670 A | 11/1987 | Andersen et al. | |
| 4,716,901 A | 1/1988 | Jackson et al. | |
| 4,738,666 A | 4/1988 | Fuqua | |
| 4,739,762 A | 4/1988 | Palmaz | |
| 4,753,636 A | 6/1988 | Free | |
| 4,772,266 A | 9/1988 | Groshong | |
| 4,798,193 A | 1/1989 | Giesy et al. | |
| 4,846,791 A | 7/1989 | Hattler et al. | |
| 4,846,812 A | 7/1989 | Walker et al. | |
| 4,865,593 A | 9/1989 | Ogawa et al. | |
| 4,869,717 A | 9/1989 | Adair | |
| 4,888,000 A | 12/1989 | McQuilkin et al. | |
| 4,896,669 A | 1/1990 | Bhate et al. | |
| 4,899,729 A | 2/1990 | Gill et al. | |
| 4,921,479 A | 5/1990 | Grayzel | |
| 4,931,042 A * | 6/1990 | Holmes et al. | 604/164.12 |
| 4,941,874 A | 7/1990 | Sandow et al. | |
| 4,954,126 A | 9/1990 | Wallsten | |
| 4,955,895 A | 9/1990 | Sugiyama et al. | |
| 4,972,827 A | 11/1990 | Kishi et al. | |
| 4,986,830 A | 1/1991 | Owens et al. | |
| 4,996,583 A | 2/1991 | Hatada | |
| 4,998,539 A | 3/1991 | Delsanti | |
| 5,021,241 A | 6/1991 | Yamahira et al. | |
| 5,041,093 A | 8/1991 | Chu | |
| 5,045,056 A | 9/1991 | Behl | |
| 5,069,674 A | 12/1991 | Fearnot et al. | |
| 5,100,388 A | 3/1992 | Behl et al. | |
| 5,112,304 A | 5/1992 | Barlow et al. | |
| 5,116,318 A | 5/1992 | Hillstead | |
| 5,122,122 A | 6/1992 | Allgood | |
| 5,139,511 A | 8/1992 | Gill et al. | |
| 5,147,316 A * | 9/1992 | Castillenti | 604/164.04 |
| 5,158,545 A | 10/1992 | Trudell et al. | |
| 5,183,464 A | 2/1993 | Dubrul et al. | |
| 5,188,602 A | 2/1993 | Nichols | |
| 5,197,971 A | 3/1993 | Bonutti | |
| 5,201,756 A | 4/1993 | Horzewski et al. | |
| 5,222,938 A | 6/1993 | Behl | |
| 5,222,971 A | 6/1993 | Willard et al. | |
| 5,226,899 A | 7/1993 | Lee et al. | |
| 5,230,702 A | 7/1993 | Lindsay et al. | |
| 5,234,425 A | 8/1993 | Fogarty et al. | |
| 5,246,424 A | 9/1993 | Wilk | |
| 5,250,025 A | 10/1993 | Sosnowski et al. | |
| 5,250,033 A | 10/1993 | Evans et al. | |
| 5,275,611 A | 1/1994 | Behl | |
| 5,279,554 A | 1/1994 | Turley | |
| 5,304,119 A | 4/1994 | Balaban et al. | |
| 5,312,360 A | 5/1994 | Behl | |
| 5,312,417 A | 5/1994 | Wilk | |
| 5,315,985 A * | 5/1994 | Decarie et al. | 600/101 |
| 5,316,360 A | 5/1994 | Feikema | |
| 5,318,588 A | 6/1994 | Horzewski et al. | |
| 5,320,611 A | 6/1994 | Bonutti et al. | |
| 5,380,290 A | 1/1995 | Makower et al. | |
| 5,392,766 A | 2/1995 | Masterson et al. | |
| 5,403,278 A | 4/1995 | Ernst et al. | |
| 5,407,430 A | 4/1995 | Peters | |
| 5,409,498 A * | 4/1995 | Braddock et al. | 606/143 |
| 5,431,676 A | 7/1995 | Dubrul et al. | |
| 5,433,708 A | 7/1995 | Nichols et al. | |
| 5,437,631 A | 8/1995 | Janzen | |
| 5,453,094 A * | 9/1995 | Metcalf et al. | 604/164.09 |
| 5,454,790 A | 10/1995 | Dubrul | |
| 5,458,579 A * | 10/1995 | Chodorow et al. | 604/164.11 |
| 5,460,170 A | 10/1995 | Hammerslag | |
| 5,484,403 A | 1/1996 | Yoakum et al. | |
| 5,487,739 A | 1/1996 | Aebischer et al. | |
| 5,496,292 A | 3/1996 | Burnham | |
| 5,540,658 A | 7/1996 | Evans et al. | |
| 5,542,928 A | 8/1996 | Evans et al. | |
| 5,556,376 A | 9/1996 | Yoon | |
| 5,569,200 A | 10/1996 | Umeno et al. | |
| 5,573,517 A | 11/1996 | Bonutti et al. | |
| 5,674,240 A | 10/1997 | Bonutti et al. | |
| 5,688,286 A * | 11/1997 | Yoon | 606/185 |
| 5,713,867 A | 2/1998 | Morris | |
| 5,800,390 A | 9/1998 | Hayakawa et al. | |
| 5,814,058 A | 9/1998 | Carlson et al. | |
| 5,827,319 A | 10/1998 | Carlson et al. | |
| 5,836,913 A | 11/1998 | Orth et al. | |
| 5,885,217 A | 3/1999 | Gisselberg et al. | |
| 5,938,587 A | 8/1999 | Taylor et al. | |
| 5,938,645 A | 8/1999 | Gordon | |
| 5,961,499 A | 10/1999 | Bonutti et al. | |
| 6,080,174 A | 6/2000 | Dubrul et al. | |
| 6,090,072 A | 7/2000 | Kratoska et al. | |
| 6,095,967 A | 8/2000 | Black et al. | |
| 6,245,052 B1 | 6/2001 | Orth et al. | |
| 6,325,789 B1 | 12/2001 | Janzen et al. | |
| 6,325,812 B1 | 12/2001 | Dubrul et al. | |
| 6,338,730 B1 | 1/2002 | Bonutti et al. | |
| 6,340,358 B1 * | 1/2002 | Bohannon et al. | 604/264 |
| 6,425,908 B2 | 7/2002 | Ravenscroft et al. | |
| 6,428,550 B1 | 8/2002 | Vargas et al. | |
| 6,450,989 B2 | 9/2002 | Dubrul et al. | |
| 6,494,893 B2 | 12/2002 | Dubrul et al. | |
| 2001/0039430 A1 * | 11/2001 | Dubrul et al. | 606/185 |
| 2002/0035373 A1 | 3/2002 | Carlson et al. | |
| 2002/0188294 A1 * | 12/2002 | Couture et al. | 606/51 |

FOREIGN PATENT DOCUMENTS

| | | |
|---|---|---|
| EP | 0 385 920 | 9/1990 |
| GB | 2199247 | 7/1988 |
| WO | WO 92/19312 | 11/1992 |
| WO | WO 95/30374 | 11/1995 |
| WO | WO 98/19730 | 5/1998 |
| WO | 98/29026 | 7/1998 |
| WO | WO 99/06094 | 2/1999 |
| WO | WO 03011154 | 2/2003 |

OTHER PUBLICATIONS

Product brochure Dexide® Inc., Dexide, Inc. (1992) 1 pg.
Product brochure Endomed™. Cooper Surgical Inc. (1992) 2 pgs.
Expando HR, Self-Fitting Protective Oversleeve, High Temperature UL Recognized VW-1 Sleeving, BentleyHarris, (1988) 2 pages.
Expando HR, Self-Fitting Protective Oversleeve, Easy-on Sleeving to Protect and Dress Wiring and Hose Assemblies, BentleyHarris, (1988) 2 pages.
Expando, Self-Fitting Protective Oversleeve, BentleyHarris, 8 pages.

* cited by examiner

TROCAR INSERTION APPARATUS

CROSS-REFERENCE TO RELATED APPLICATIONS

The present application claims the benefit of and priority to U.S. Provisional Application Ser. No. 60/504,506, filed on Sep. 19, 2003, the entire disclosure of which is incorporated herein by reference.

BACKGROUND

1. Technical Field

The present disclosure relates to surgical apparatus for facilitating the insertion of surgical instruments into a body cavity of a patient and, more particularly, to surgical apparatus adapted to facilitate the insertion of an expansion assembly (i.e., a trocar) through a radially expandable dilation assembly and into the body cavity of the patient.

2. Background of Related Art

Minimally invasive surgical procedures are performed throughout the body and generally rely on obtaining percutaneous access to an internal surgical site using small diameter tubes (typically 5 to 12 mm), usually referred to as cannulas, which provide access through the skin of the patient and open adjacent the desired surgical site. A viewing scope is introduced through one such cannula, and the surgeon operates using instruments introduced through other appropriately positioned cannulas while viewing the operative site on a video monitor connected to the viewing scope. The surgeon is thus able to perform a wide variety of surgical procedures requiring only a few 5 to 12 mm punctures through the patient's skin, tissue, etc. adjacent the surgical site.

Certain minimally invasive surgical procedures are often named based on the type of viewing scope used to view the area of the body which is the operative site. For example, laparoscopic procedures use a laparoscope to view the operative site and are performed in the interior of the abdomen through a small incision. Such laparoscopic procedures typically require that a gas, such as carbon dioxide, be introduced into the abdominal cavity. This establishes pneumoperitoneum wherein the peritoneal cavity is sufficiently inflated for the insertion of trocars into the abdomen.

Pneumoperitoneum is established through the use of a special insufflation needle, called a Veress needle, which has a spring-loaded obturator that advances over the sharp tip of the needle as soon as the needle enters the abdominal cavity. This needle is inserted through the fascia and through the peritoneum. Generally, the surgeon relies on tactile senses to determine the proper placement of the needle by recognizing when the needle is inserted through the fascia and then through the peritoneum. After establishing pneumoperitoneum, the next step in laparoscopic surgery involves the insertion of a trocar, obturator or trocar/obturator assembly into the abdominal cavity.

Preferably, the cannulas used in laparoscopic procedures should be readily sealable to inhibit the leakage of the insufflation gas from the abdominal cavity, in particular, should be designed to inhibit leakage from the region between the external periphery of the trocar and the abdominal wall.

In order to reduce the amount of insufflation gas which escapes from the abdominal cavity, a radially expandable access system has been developed to provide improved sealing about the periphery of the cannula. A system for performing such a function is commercially available from United States Surgical, a division of Tyco Healthcare, Ltd. under the trademark VERSASTEP™. Certain aspects of the expandable access system are described in commonly assigned U.S. Pat. Nos. 5,431,676; 5,814,058; 5,827,319; 6,080,174; 6,245,052 and 6,325,812, the entire contents of which are expressly incorporated herein by reference.

As disclosed therein, the expandable access system includes a sleeve having a sleeve body, typically made up of a radially expandable braid covered by an elastomeric layer. The braid initially has an inner diameter of about 2 mm and an outer diameter of about 3.5 mm. In use, passage of a surgical instrument (i.e., trocar, cannula, obturator, etc.) through the expandable access system causes radial expansion of the sleeve, typically to a final diameter of 5 mm, 10 mm or 12 mm. However, the sleeve can be expanded to any necessary diameter in order to accommodate the particular surgical instrument. The expandable access system further includes a handle affixed to a proximal end of the sleeve, the handle including a passage formed therein for the introduction of surgical instruments, through the handle, into the sleeve body.

A method of use of the expandable sealing apparatus includes inserting a pneumoperitoneum needle through the radially expandable sleeve body of the expandable access system to thereby form a needle/sleeve assembly. The needle/sleeve assembly is then introduced through the patient's abdomen by engaging the sharpened distal end of the pneumoperitoneum needle, protruding from the distal end of the sleeve body, against the body tissue of the body cavity and advancing the needle/sleeve assembly into the body cavity until the needle/sleeve assembly extends across the layers of the body tissue thereby forming an incision in the body tissue. The pneumoperitoneum needle is then removed from the body of the sleeve. A cannula, having a diameter smaller than the opening in the handle and larger than the lumen of the sleeve, is then introduced through the opening in the handle and into the abdomen of the patient. As a result, due to radial expansion of the sleeve by the trocar, the incision is subsequently also radially expanded. Cannulas used in laparoscopic procedures include a valve at a proximal end thereof in order to permit passage of a trocar, viewing scope or other surgical instrument therethrough while simultaneously inhibiting escape of insufflation gas from the abdominal cavity.

Accordingly, there exists a need for an expansion assembly insertion apparatus which facilitates and enhances control of the insertion of and expansion assembly into the axial lumen of a radially expandable dilation assembly and into the abdominal cavity of the patient.

SUMMARY

Apparatus for forming and enlarging a percutaneous penetration are disclosed. According to one aspect of the present disclosure, the apparatus includes an elongate dilation member including a radially expandable member having a proximal end with a handle, a distal end, and an axial lumen with a first cross-sectional area; and an elongate expansion member including a tubular element having a distal end, a proximal end with a handle, and an axial lumen with a second cross-sectional area which is larger than the first cross-sectional area. The distal end of the expansion member is configured for facilitating insertion of the tubular element through the axial lumen of the dilation member. The apparatus further includes an advancing apparatus having a first arm with a first engaging feature for engaging the handle of the dilation member; a second arm with a second engaging feature for engaging the handle of the expansion member; and an operation member. The first arm and the second arm are connected so that operation of the operation member approximates the first engaging feature and the second engaging feature together.

It is envisioned that the radially expandable member includes a braided sleeve. It is further envisioned that the radially expandable member includes a splittable sheath.

Desirably, the operation member is attached to the second arm. The second arm may include a passage for receiving the first arm. The operation member may be pivotally attached to the second arm and may have a pivotal link engaging the first arm so that upon pressing the operation member, the link moves the first arm proximally.

Desirably, the first arm extends parallel to the longitudinal axes of the dilation member and the expansion member. It is contemplated that the first arm and the second arm may include inter-engaging ratchet teeth. It is further contemplated that the first arm and the second arm may be pivotally attached so that pressing the operation member toward the first arm approximates the first engaging feature and second engaging feature together.

According to another aspect of the present disclosure, an apparatus for facilitating the insertion of an expansion assembly distally through a radially expandable dilation assembly into a body cavity of a patient is provided. The apparatus includes a handle; and a trigger operatively coupled to the handle. The trigger is pivotable between a first position, spaced a distance from the handle, and a second position, in close proximity to the handle. The apparatus further includes a spine member having a proximal end and a distal end. The spine member is slidably received within the handle and is axially moveable relative to the handle upon a manipulation of the trigger from the open position to the closed position.

The apparatus further includes an actuation mechanism in operative engagement with the handle, the trigger and the spine member. The actuation mechanism is releasably engagable with the spine member and, when engaged with the spine member, axially moves the spine member relative to the handle upon movement of the trigger to the closed position. The apparatus further includes an expansion assembly retaining structure operatively coupled to the handle for holding the expansion assembly in place; and a yoke provided at the distal end of the spine member for maintaining the dilation assembly aligned with the expansion assembly.

Desirably, manipulation of the trigger towards the handle incrementally approximates the yoke toward the expansion assembly retaining structure.

It is envisioned that the yoke defines a distal clevis and a proximal clevis. Accordingly, tabs extending from opposite sides of a handle of the dilation assembly are positionable between the distal clevis and the proximal clevis. It is further envisioned that the expansion assembly retaining structure includes at least one C-shaped cuff configured to operatively engage a handle of the expansion assembly in a snap-fit manner.

The actuation mechanism may include a driving lever operatively supported on the spine member; a linkage member having a first end pivotally connected to the trigger and a second end slidably received within the handle and pivotally connected to the driving lever; and a compression spring disposed between the driving lever and an inner surface of the handle. The compression spring desirably biases the driving lever to an orientation orthogonal to the spine member. Accordingly, actuation of the trigger toward the handle causes the driving lever to pivot and bind against the spine member.

The actuation mechanism may further include a braking lever operatively supported on the spine member, a first end of braking lever is pivotally positioned within a recess formed in the handle; and a spring member disposed between braking lever and a surface formed in the handle, wherein the spring member biases a free end of the braking lever in a distal direction.

It is envisioned that the proximal end of the spine member may extend from a proximal end of the handle.

The apparatus may include an elongate dilation assembly operatively associatable with the yoke. The elongate dilation assembly may include a handle, a radially expandable tubular sheath having a proximal end connected to the handle, a distal end, and defining an axial lumen with a first cross-sectional area. The apparatus may further include an elongate expansion assembly operatively connectable to the at least one cuff. The expansion assembly may include a tubular element having a distal end, a proximal end with a handle, and an axial lumen with a second cross-sectional area which is larger than the first cross-sectional area of the elongate dilation assembly.

According to another aspect of the present disclosure, a kit for providing access to a target surgical site is provided. The kit includes a radially expandable dilation assembly; a pneumoperitoneum needle assembly; a stylet; an expansion assembly; an obturator; an expansion assembly insertion apparatus for forming and enlarging a percutaneous penetration; and a package for enclosing the radially expandable dilation assembly, the pneumoperitoneum needle assembly, the stylet, the expansion assembly, the obturator, and the expansion assembly insertion apparatus.

The kit may further include a package insert including at least one of instructions on use and warnings of use.

Other features and advantages of the disclosed trocar insertion apparatus will appear from the following description in which the preferred embodiment has been set forth in conjunction with the accompanying drawings.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Preferred embodiments of the presently disclosed expansion assembly insertion apparatus will now be described in detail with reference to the drawing figures wherein like reference numerals identify similar or identical elements. In the drawings and in the description which follows, the term "proximal", as is traditional will refer to the end of the surgical device or instrument of the present disclosure which is closest to the operator, while the term "distal" will refer to the end of the device or instrument which is furthest from the operator.

Figure 1:
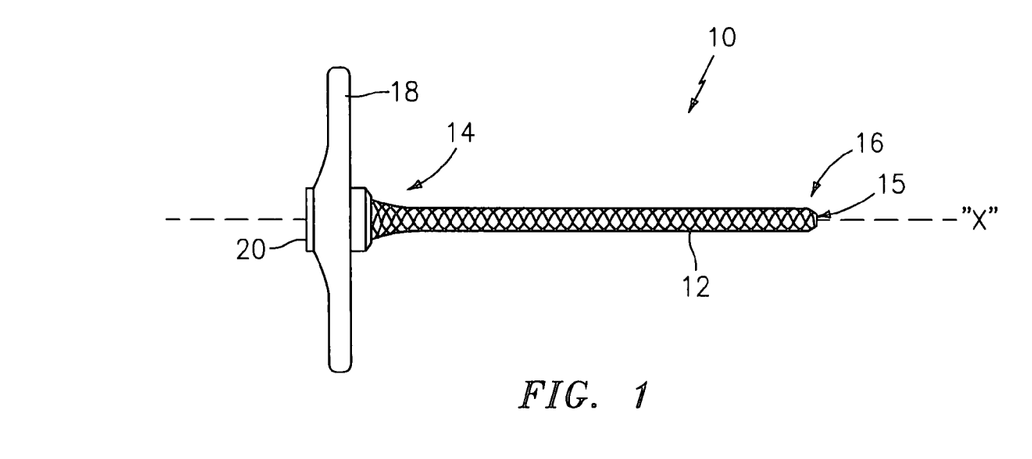
FIG. 1 is a side elevational view of a radially expandable dilation assembly for sealing a percutaneous opening in a patient.

Referring now in detail to the drawing figures, as seen in FIG. 1, a radially expandable dilation assembly is generally designated with the reference numeral 10. Radially expandable dilation assembly 10 includes a tubular sheath 12 having a proximal end 14, a distal end 16 and an axial lumen 15 extending therethrough. Axial lumen 15 defines a longitudinal axis "X" and further defines a first cross-sectional area extending therethrough. Proximal end 14 is tapered radially outward in the proximal direction and is secured to a handle 18. Handle 18 includes an aperture 20 extending therethrough and interconnected with lumen 15 of tubular sheath 12. Tubular sheath 12 may be made from any material which is capable of receiving an expansion assembly to effect radial expansion of sheath 12, as described in more detail hereinafter.

Sheath 12 preferably includes an inelastic braid covered by an elastic membrane, as described in commonly assigned U.S. Pat. No. 5,431,676, the full disclosure of which is incorporated herein by reference. Suitable expandable sleeves 10 may be obtained commercially from United States Surgical, a division of Tyco Healthcare, Ltd., as part of the STEP™ introducer system.

Figure 2:
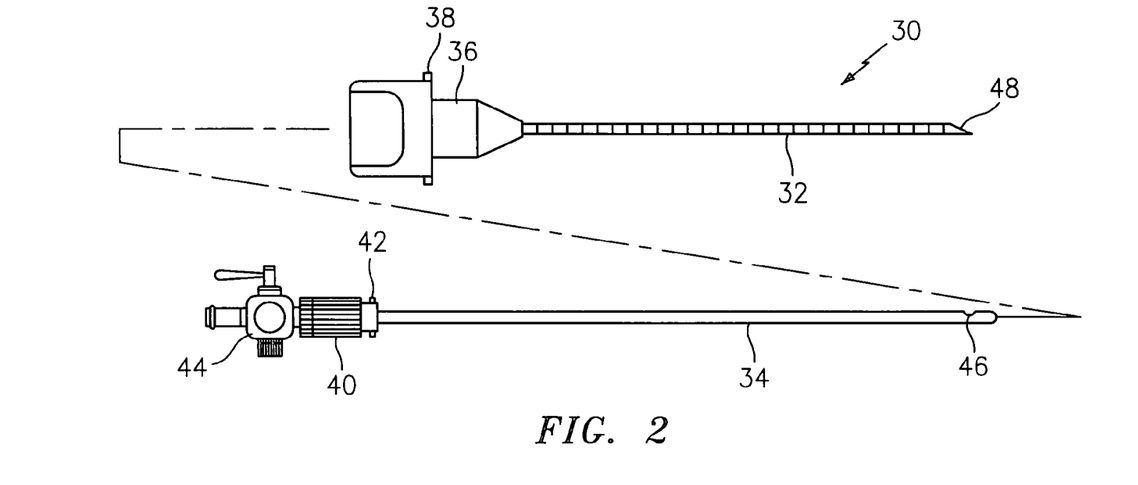
FIG. 2 is a side elevational view of a pneumoperitoneum needle component of the dilation assembly, shown with a stylet removed from a tubular needle body.

A pneumoperitoneum needle assembly 30 including a tubular needle 32 and a stylet 34 is illustrated in FIG. 2. Tubular needle 32 includes a hub 36 having a male bayonet connector 38 at a proximal end thereof. Preferably, stylet 34 is spring loaded in a proximal connector 40 which includes a male bayonet fitting 42. Male bayonet fitting 42 is receivably coupled to female bayonet fitting (not illustrated) of hub 36. An insufflation valve 44 is connected to the proximal end of stylet 34 and a port 46 is formed in a distal end thereof. Port 46 permits the introduction of insufflation gas through valve 44 to be released through stylet 34. In use, stylet 34 is mounted within needle 32 with bayonet fitting 42 attached to hub 36. The distal end of stylet 34 in turn extends from a distal end 48 of needle 32 such that stylet 34 will retract into needle 32 when needle assembly 30 is engaged against tissue, as described in more detail below.

Figure 3:
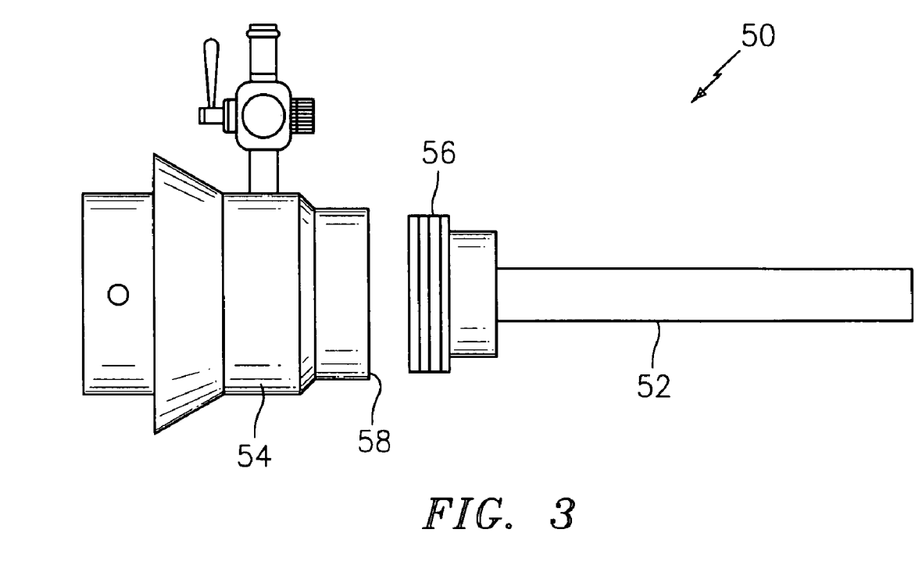
FIG. 3 is a partly separated side elevational view of a cannula assembly of an elongate expansion assembly.

Referring now to FIG. 3, an expansion assembly 50 is shown and described. Expansion assembly 50 includes an expansion member 52 (i.e., a cannula tube) and a proximal hub 54. Expansion member 52 includes a threaded connector 56 at its proximal end which can be removably secured to a fitting 58 in the distal end of proximal hub 54. Preferably, expansion member 52 defines a second cross-sectional area which is larger than the first cross-sectional area of tubular sheath 12.

Figure 4:
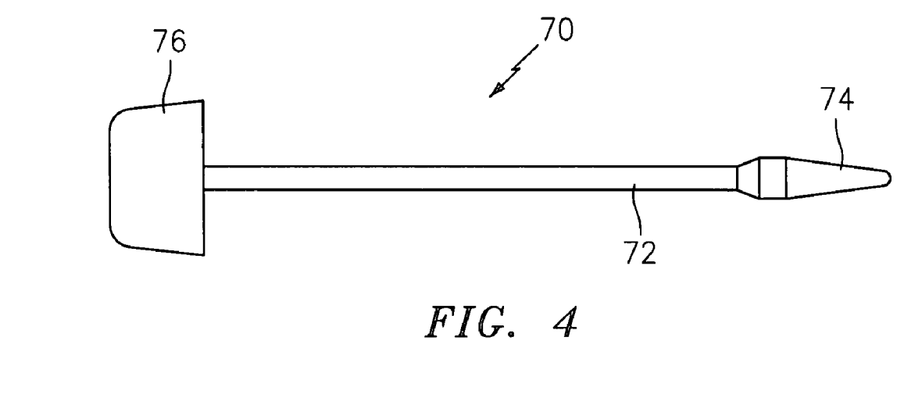
FIG. 4 is a side elevational view of an obturator component for use with the elongate expansion assembly of FIG. 3.

With reference to FIG. 4, an obturator 70 including a shaft 72 having a tapered distal end 74 (see also FIGS. 5, 8, and 9) and a handle 76 is shown and described. As will be described in greater detail below, obturator 70 is intended to be placed within a central lumen of cannula assembly 50 in order to facilitate insertion of expansion assembly 50 into radially expandable dilation assembly 10.

Figure 5:
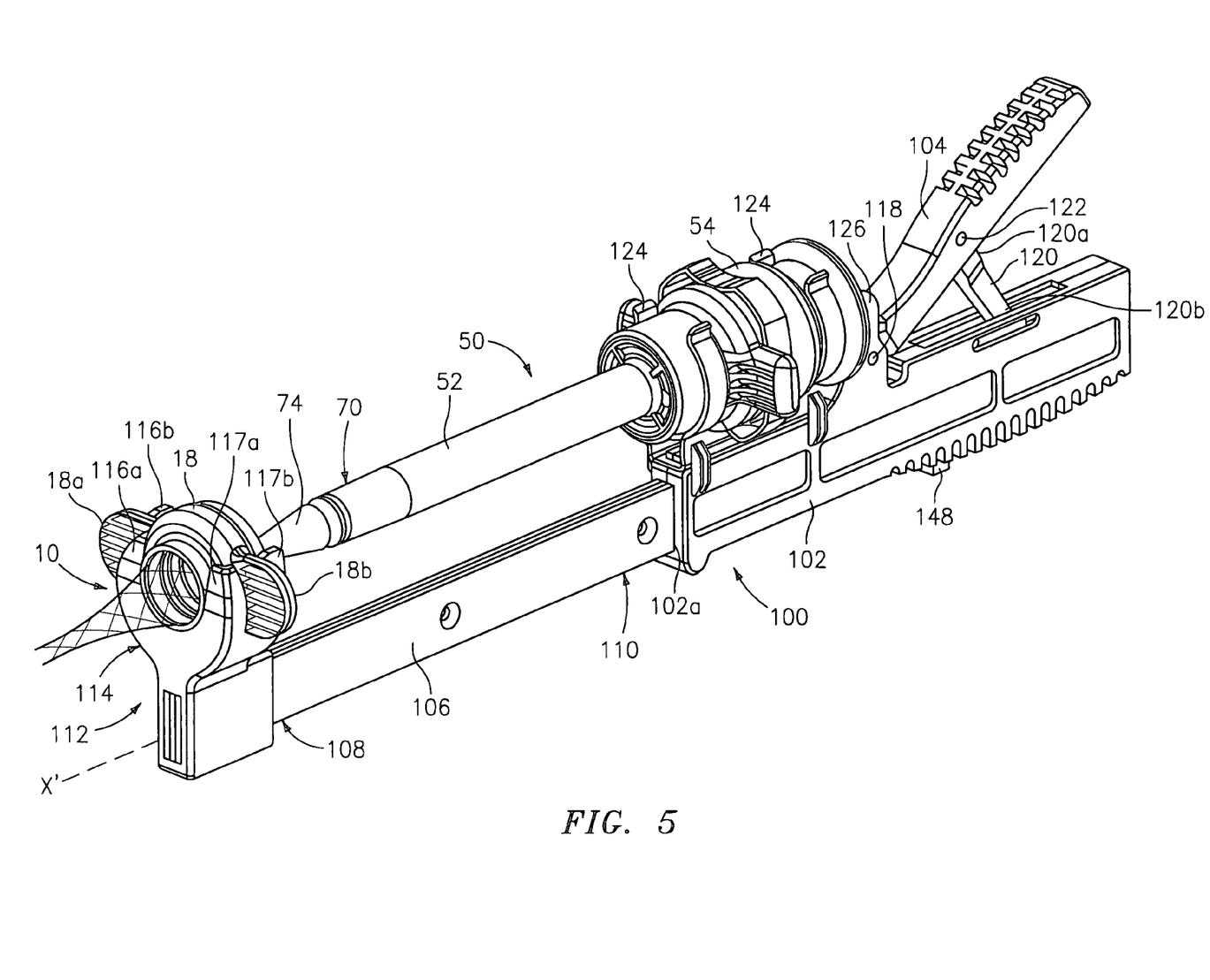
FIG. 5 is a perspective view of an expansion assembly insertion apparatus, in accordance with the present disclosure, having an expansion assembly and a dilation assembly operatively mounted thereto.

Turning now to FIG. 5, an expansion assembly insertion apparatus in accordance with the present disclosure, having an expansion assembly 50 and a dilation assembly 10 operatively mounted thereto, is shown generally as reference numeral 100. Insertion apparatus 100 includes a proximally extending fixed handle 102, a trigger 104 pivotably coupled to fixed handle 102 at pivot pin 118, and a distally extending spine member 106. Spine member 106 has a distal end 108 and a proximal end 110 defining a longitudinal axis "X". Proximal end 110 of spine member 106 is slidably received within fixed handle 102 through an aperture 102a formed in a distal end of fixed handle 102. While a generally rectangular cross-section for spine member 106 has been depicted it is contemplated that spine member 106 can have a circular, elliptical, square or other polygonal cross-section.

Distal end 108 of spine member 106 is provided with a yoke or engaging feature 112 operatively coupled thereto. Yoke 112 defines a U-shaped clevis 114 having a pair of legs 116, 117. Preferably, clevis 114 includes a distal pair of legs 116a, 117a and a proximal pair of legs 116b, 117b. Legs 116, 117 define an axis which is substantially parallel to the longitudinal "X" axis of spine member 106. In use, U-shaped clevis 114 of yoke 112 receives handle 18 of dilation assembly 10 therein. In particular, handle 18 includes a pair of diametrically opposed tabs 18a, 18b wherein either tab 18a or 18b is positioned between distal and proximal legs 116a and 116b while the other of tab 18a or 18b is positioned between distal and proximal legs 117a and 117b.

Figure 6:
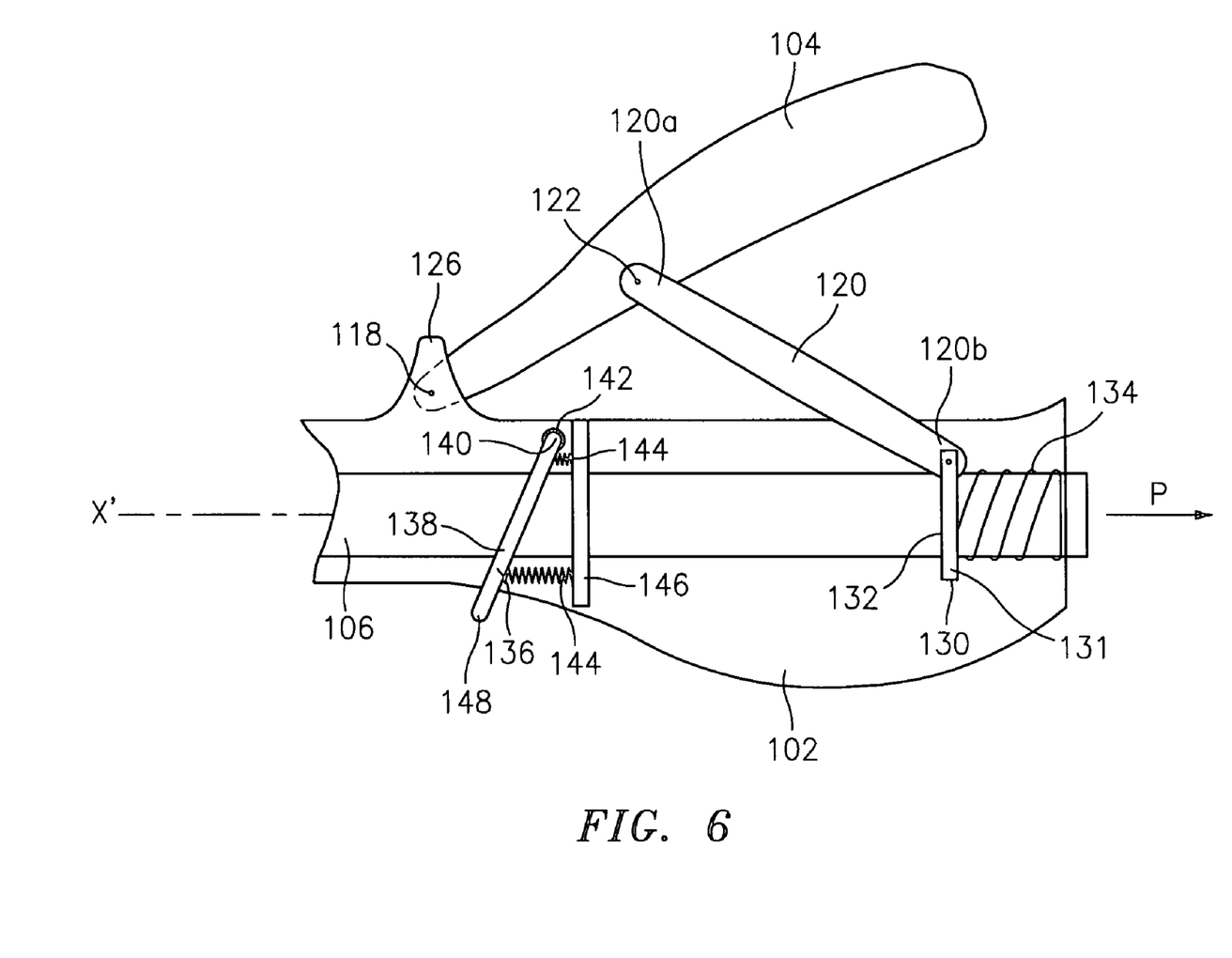
FIG. 6 is a cross-sectional side elevational view of the fixed handle and trigger of the expansion assembly insertion apparatus, taken along the longitudinal axis thereof, illustrating an exemplary actuation mechanism.

As best seen in FIG. 6, fixed handle 102 includes an actuation mechanism for the mechanical operation of insertion apparatus 100. The actuation mechanism includes a linkage member 120 having a first end 120a which is pivotably coupled to trigger 104 at a pivot point 122 and a second end 120b which is slidably received within fixed handle 102 and pivotably coupled to a driving lever 130.

Driving lever 130 is located and/or suspended on spine member 106 which passes through an aperture or opening 132 formed in driving lever 130. A compression spring 134 disposed between driving lever 130 and an inner surface of fixed handle 102 urges driving lever 130 in a distal direction and to remain orthogonal relative to spine member 106. The force of spring 134 urges trigger 104 against a backing member 126, via linkage member 120, of fixed handle 102 thus providing a standby condition. In the standby condition, driving lever 130 is positioned substantially perpendicular to the direction of motion, indicated by the arrow "P", of spine member 106 when in operation. Motion of trigger 104 about the pivot pin 118 causes spine member 106 to move against the bias of spring 134, as will be described in greater detail below.

The actuation mechanism further includes a braking lever 136 having an opening 138 through which spine member 106 passes. One end 140 of braking lever 136 is pivotably positioned in a recess 142 formed in fixed handle 102 such that braking lever 136 may pivot within constraints defined by the surfaces of recess 142 and by the binding of braking lever 136 with spine member 106 when the edges of opening 138 in braking lever 136 engage the surfaces of spine member 106. At least one compression spring 144 is disposed between a wall 146 in fixed handle 102 and braking lever 136. Spring 144 effectively biases the free end of braking lever 136 distally away from driving lever 130. The biased position of braking lever 136 is limited by the binding and/or cocking interference between opening 138 of braking lever 136 and the surfaces of spine member 106. In the embodiment illustrated in FIG. 6, braking lever 136 extends in the direction of fixed handle 102 so that its distal end 148 can be suitably gripped by the thumb of a user.

It should be noted that in the standby position illustrated in FIG. 6, driving lever 130 is substantially perpendicular to the longitudinal "X'" axis of spine member 106, whereas the portion of braking lever 136 which engages spine member 106 is transversely oriented to the longitudinal "X'" of spine member 106 at a slight angle. In this condition, if a force is applied to yoke 112 (FIG. 5) in the direction indicated by arrow "P", slide member 106 is free to move through fixed handle 102. Since braking lever 136 is free to pivot against the bias of spring 144 when force is applied on yoke 112, in the direction of arrow "P", braking lever 136 presents no obstacle to the motion of spine member 106 and yoke 112 and thus may be advanced continuously through fixed handle 102.

However, in the standby position, as illustrated in FIG. 6, if a force is applied to yoke 112 in the direction opposite to the direction indicated by arrow "P", the edges of opening 138 in braking lever 136 bind against the surfaces of spine member 106 and it is not possible to withdraw the moving yoke 112 further away from fixed handle 102. Compression of spring 144, by pressing on braking lever 136 with a finger in the direction of the arrow "P", allows withdrawal of spine member 106 and yoke 112 to be extended away from fixed handle 102. Compression of spring 144 brings distal end 148 of braking lever 136 into perpendicularity with the direction of intended motion of spine member 106, and thus spine member 106 is then free to slide in either direction through opening 136 in braking lever 136.

The preferred method of use of expansion assembly insertion apparatus 100 is to squeeze trigger 104 (toward fixed handle 102) to incrementally advance spine member 106 and yoke 112 through fixed handle 102. When trigger 104 is squeezed, pivoting occurs about pivot pin 118 and second end 120b of linkage member 120 also moves substantially in the direction of arrow "P". This causes driving lever 130 to pivot about its first end 131 so that driving lever 130 is no longer perpendicular to the direction "P" of intended motion of spine member 106. Pivoting of driving lever 130 compresses spring 134 and also causes the end edges of aperture 132, formed in driving lever 130 to bind against the surfaces of spine member 106. Binding occurs because driving lever 130 is no longer perpendicular to the direction "P" of intended motion of spine member 106. Further motion of trigger 104 causes driving lever 130 to translate in the direction of arrow "P". This motion further compresses spring 134 and in the process, by means of the binding and/or cocking interference between driving lever 130 and spine member 106, advances spine member 106 and its connected yoke 112 through fixed handle 102. The maximum distance of advancement of yoke 112, with one squeeze of trigger 104, is limited to when spring 134 is fully compressed or trigger 104 strikes the surface of fixed handle 102.

After trigger 104 is fully pivoted about pivot pin 118, release of trigger 104 causes the return of trigger 104 to the stand by condition due to spring 134 urging driving lever 130 to a perpendicular position and pressing linkage member 120 into trigger 104.

Returning to FIG. 5, fixed handle 102 is further provided with at least one, preferably a pair of resilient C-shaped cuffs 124 affixed to a distal end thereof. Cuffs 124 define a longitudinal axis which is substantially aligned with the axis of clevis 114 defined by legs 116, 117. In use, cuffs 124 are configured to receive proximal hub 54 of cannula assembly 50 therein by a snap-fit type engagement.

In addition, fixed handle 102 is provided with a backing member 126 as described above. Backing member 126 preferably extends transversely from fixed handle 102 beyond the longitudinal axis of cuffs 124. Accordingly, in operation, backing member 126 preferably acts as a stop for a proximal end surface of expansion assembly 50 when expansion assembly 50 is mounted to expansion assembly insertion apparatus 100.

While insertion apparatus 100 has been shown and described herein as including a trigger 104 for incrementally approximating clevis 114 toward cuffs 124, it is envisioned and within the scope of the present disclosure that any operation member may be used to accomplish that same function. For example, the operation member may include a ratchet mechanism, a screw drive, a pneumatic drive or the like to advance clevis 114 toward cuffs 124.

Figures 7, 8:
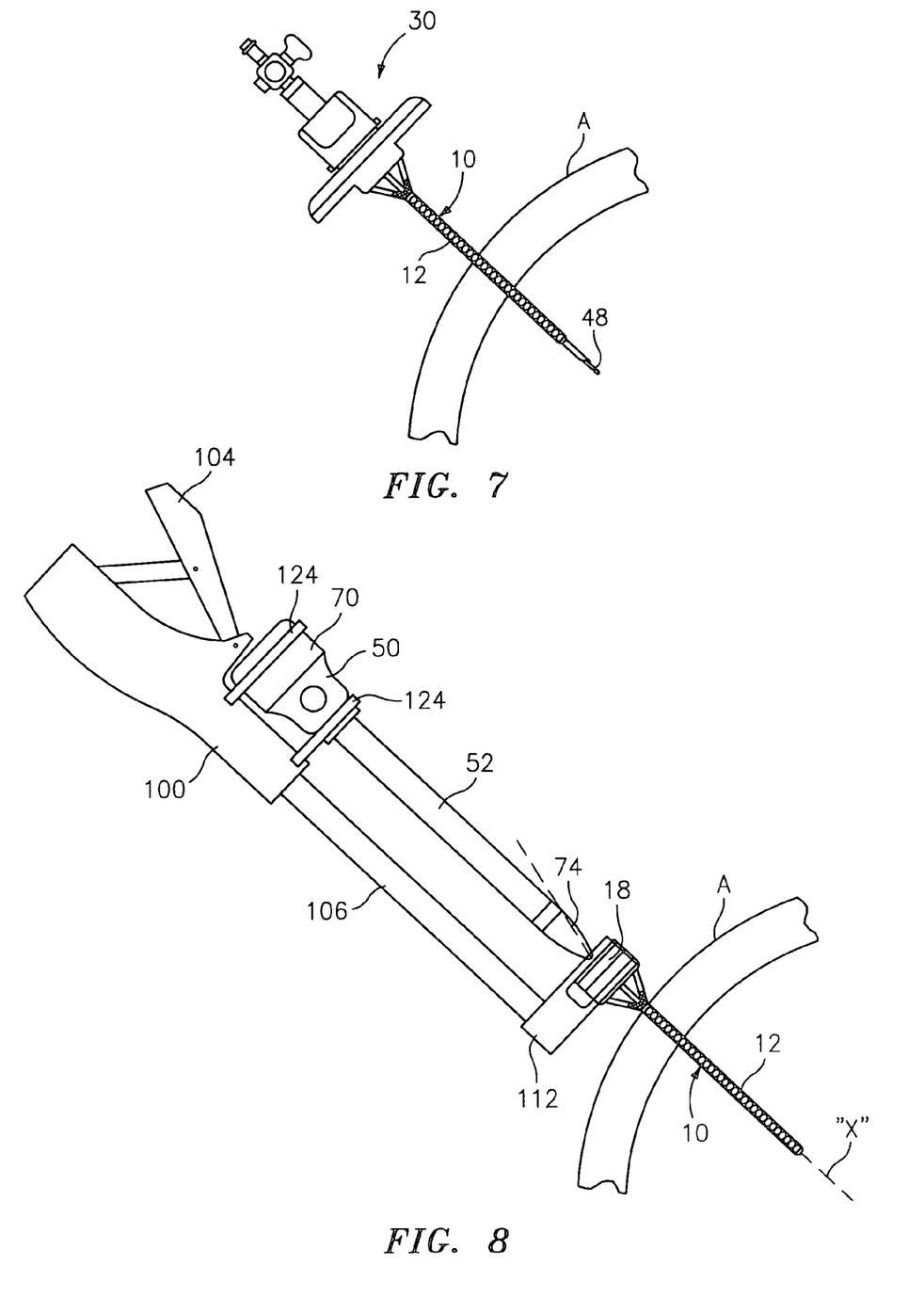
FIGS. 7-10 illustrate use of the expansion assembly insertion apparatus in connection with the dilation assembly of FIG. 1 and the expansion assembly of FIG. 2 for facilitating insertion of the expansion assembly in to the dilation assembly.

Referring now to FIGS. 7-10, a preferred method of operation of expansion assembly insertion apparatus 100, will be described. Initially, as seen in FIG. 7, the radially expandable dilation assembly 10, having pneumoperitoneum needle assembly 30 inserted therein, is introduced through a patient's abdomen "A" (or other body location) by engaging sharpened distal end 48 of needle assembly 30 against the tissue of the patient's abdomen "A" and advancing the sleeve/needle combination forward until tubular sheath 12 of dilation assembly 10 extends across the tissue of abdomen "A".

Figure 9:
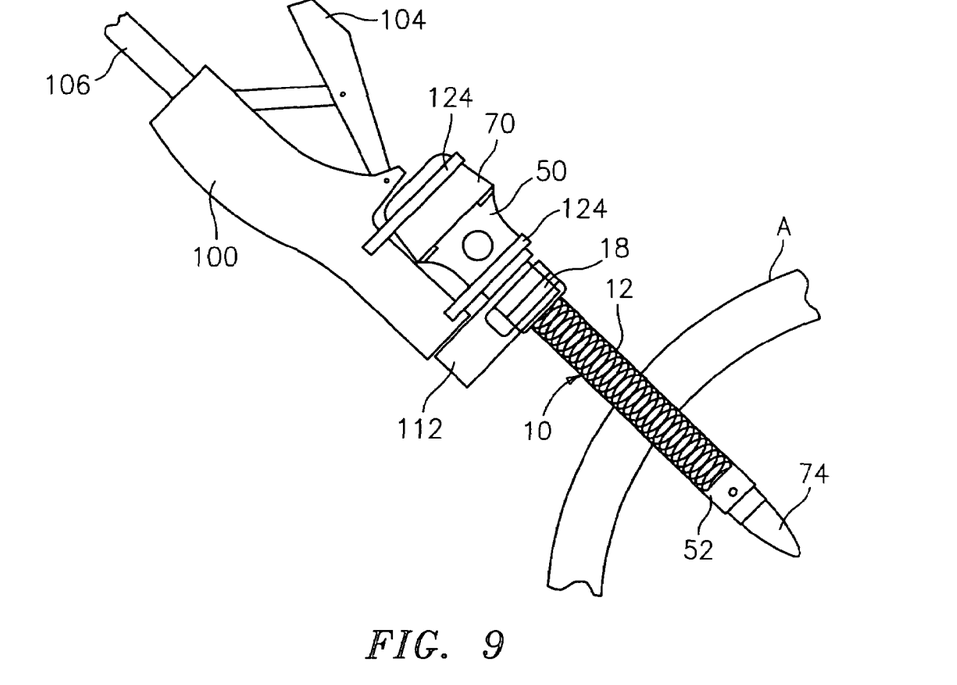

Needle assembly 30 is then removed, and an expansion assembly 50 including an obturator 70 disposed therewithin is introduced through tubular sheath 12 of dilation assembly 10, with the aid of expansion assembly insertion apparatus 100 thereby resulting in radial expansion of tubular sheath 12 (see FIG. 9). In particular, yoke 112 of insertion apparatus 100 is preferably first hooked onto handle 18 of dilation assembly 10 as described above. Next, expansion assembly 50, including obturator 70, is loaded into insertion apparatus 100 by coupling proximal hub 54 of expansion assembly 50 to cuffs 124 as described above. Finally, insertion apparatus 100 is actuated by repeatedly squeezing trigger 104, as described above, in order to incrementally advance expansion assembly 50 and obturator 70 through dilation assembly 10. As expansion assembly 50 and obturator 70 are moved distally through tubular sheath 12, dilation assembly 10 is radially expanded from the first cross-sectional area to the second cross-sectional area.

Figure 10:
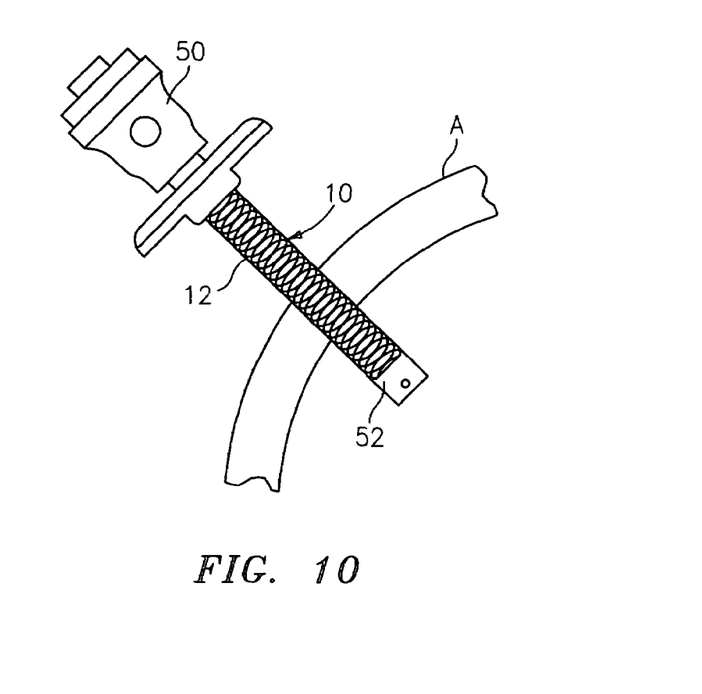

Finally, as illustrated in FIG. 10, obturator 70 is removed from expansion member 52, leaving an access channel through abdominal wall "A" for the introduction of a variety of other surgical instruments through the access channel.

An ergonomic feature of insertion apparatus 100 is the substantially longitudinally oriented fixed handle 102 and trigger 104. In other words, fixed handle 102 is preferably aligned with the longitudinal axis of spine member 106 while trigger 104 is preferably pivotable to a closed position which is substantially aligned with the longitudinal axis of spine member 106. Thus, the longitudinal axis of insertion apparatus 100 is oriented in a substantially orthogonal direction with respect to the longitudinal axis of the forearm of the surgeon. Accordingly, the application of the insertion force by the surgeon preferably occurs by the surgeon gripping fixed handle 102 and trigger 104 and pivoting his forearm about his elbow such that is hand travels in a direction substantially co-linear with the longitudinal axis of insertion apparatus 100.

Figure 11:
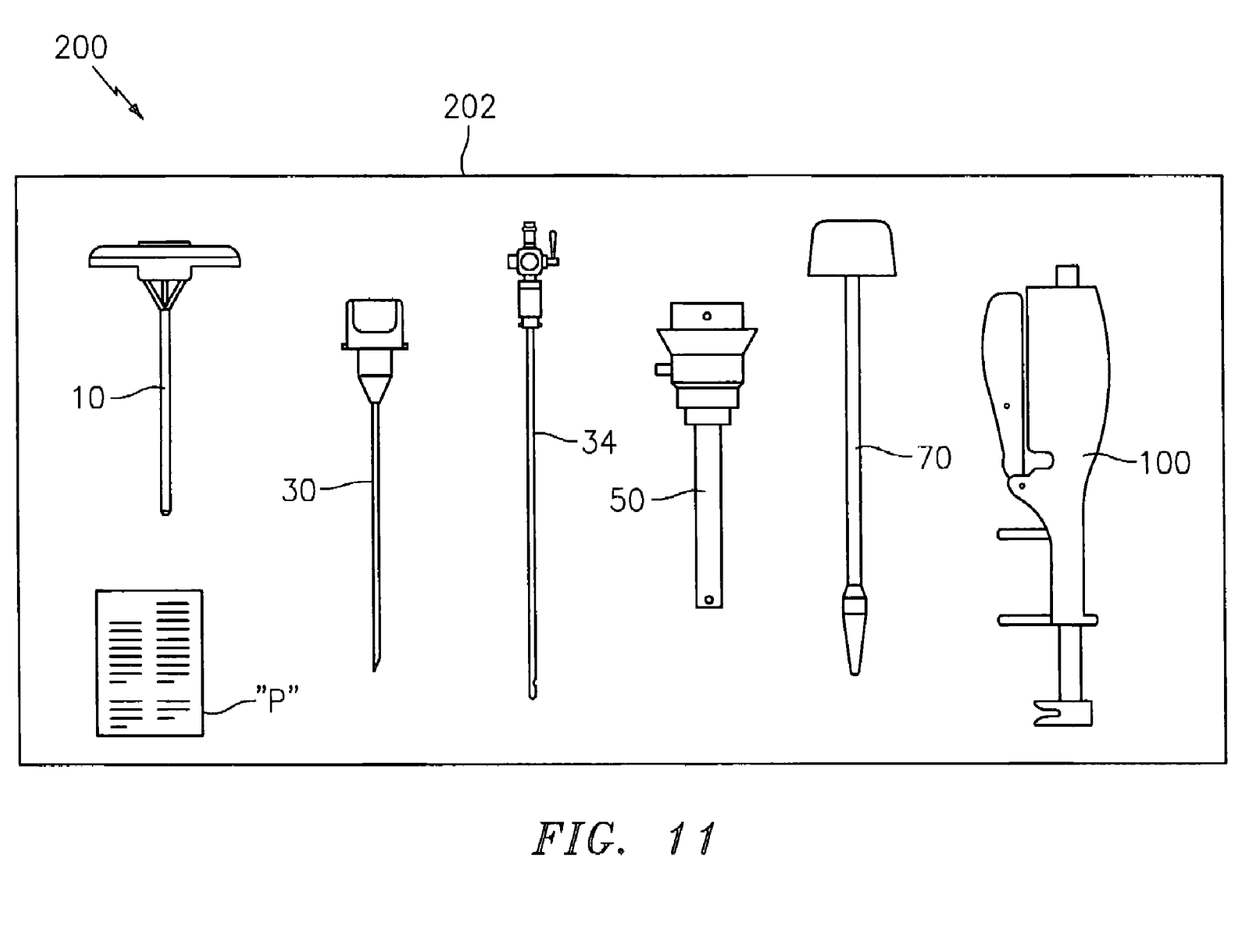
FIG. 11 illustrates a kit including a radially expandable dilation assembly, a pneumoperitoneum needle, a cannula assembly, an obturator and an insertion apparatus present in a package.

Turning now to FIG. 11, an exemplary package or "kit" containing various combinations of system components is illustrated. Providing such kits is a particularly convenient way to facilitate inventory maintenance of the components necessary to reconstruct the access systems of the present disclosure. It will be appreciated, of course, that complete systems could be sold in kits, as well as each of the individual components can be sold in their own kits. In many cases, it will be desirable to combine the pairs of components or multiple pieces of a single component together in one package, particularly where the components are sized to match each other. The kits will include conventional package elements, typically pouches, envelopes, trays, boxes, foam inserts and other containers of a type commonly used for sterile or non-sterile packaging of surgical instruments. The packages will typically also include a "package insert P" which is a written instruction sheet with instructions on use, warnings, etc.

As seen in FIG. 11, an exemplary kit 200, for providing access to a target surgical site, includes a package 202, typically non-sterile since the reusable components can be subsequently sterilized and at least one of the following items: a radially expandable dilation assembly 10; a pneumoperitoneum needle assembly 30; a stylet 34; an expansion assembly 50; and an obturator 70. Kit 200 further includes an expansion assembly insertion apparatus 100.

Although the foregoing disclosure has been described in some detail by way of illustration and example, for purposes of clarity or understanding, it will be obvious that certain changes and modifications may be practiced within the scope of the appended claims.

What is claimed is:

1. Apparatus for forming and enlarging a percutaneous penetration, the apparatus comprising:
    an elongate dilation member including a radially expandable member having a proximal end with a handle, a distal end, and an axial lumen with a first cross-sectional area;
    an elongate expansion member including a tubular element having a distal end, a proximal end with a handle, and an axial lumen with a second cross-sectional area which is larger than the first cross-sectional area;
    the distal end of the expansion member being configured for facilitating insertion of the tubular element through the axial lumen of the dilation member; and
    an advancing apparatus having:
        a first arm with a first engaging feature configured and dimensioned to selectively receive the handle of the dilation member to substantially inhibit axial movement of the dilation member relative to the first arm;
        a second arm with a second engaging feature configured and dimensioned to selectively receive the handle of the expansion member to substantially inhibit axial movement of the expansion member relative to the second arm, wherein the first arm and the second arm are configured to maintain axial alignment between the dilation member and the expansion member; and
        an operation member;
        the first arm and the second arm being connected so that operation of the operation member approximates the first engaging feature and the second engaging feature together.

2. The apparatus of claim 1, wherein the radially expandable member comprises a braided sleeve.

3. The apparatus of claim 2, wherein the radially expandable member comprises a splittable sheath.

4. The apparatus of claim 1, wherein the operation member is attached to the second arm.

5. The apparatus of claim 4, wherein the second arm includes a passage for receiving the first arm.

6. The apparatus of claim 5, wherein the operation member is pivotally attached to the second arm and has a pivotal link engaging the first arm so that upon pressing the operation member, the link moves the first arm proximally.

7. The apparatus of claim 6, wherein the first arm extends parallel to longitudinal axes of the dilation member and the expansion member.

8. The apparatus of claim 4, wherein the first arm and the second arm are slidably attached to each other so that pressing the operation member toward the first arm approximates the first engaging feature and second engaging feature together.

9. An apparatus for facilitating the insertion of an expansion assembly distally through a radially expandable dilation assembly into a body cavity of a patient, the apparatus comprising:
    a handle;
    a trigger operatively coupled to the handle, the trigger being pivotable between a first position, spaced a distance from the handle, and a second position, in close proximity to the handle;
    a spine member having a proximal end and a distal end, the spine member being slidably received within the handle, the spine member being axially moveable relative to the handle upon a manipulation of the trigger from the open position to the closed position;
    an actuation mechanism in operative engagement with the handle, the trigger and the spine member, the actuation mechanism being releasably engagable with the spine member and, when engaged with the spine member, axially moves the spine member relative to the handle upon movement of the trigger to the closed position;
    an expansion assembly retaining structure operatively coupled to the handle, the expansion assembly retaining structure being configured and dimensioned to selectively receive the expansion assembly to substantially inhibit axial movement of the expansion assembly relative to the handle; and
    a yoke provided at the distal end of the spine member, the yoke being configured and dimensioned to selectively receive the dilation assembly to substantially inhibit axial movement of the dilation assembly relative to the spine member, wherein the handle and the spine member are configured to maintain axial alignment between the expansion assembly and the dilation assembly.

10. The apparatus of claim 9, wherein manipulation of the trigger towards the handle incrementally approximates the yoke toward the expansion assembly retaining structure.

11. The apparatus of claim 10, wherein the yoke defines a distal clevis and a proximal clevis, wherein tabs extending from opposite sides of a handle of the dilation assembly are positionable between the distal clevis and the proximal clevis.

12. The apparatus of claim 11, wherein the expansion assembly retaining structure includes at least one C-shaped cuff configured to operatively engage a handle of the expansion assembly in a snap-fit manner.

13. The apparatus of claim 12, wherein the actuation mechanism includes:
    a driving lever operatively supported on the spine member;
    a linkage member having a first end pivotally connected to the trigger and a second end slidably received within the handle and pivotally connected to the driving lever; and
    a compression spring disposed between the driving lever and an inner surface of the handle, the compression spring biasing the driving lever to an orientation orthogonal to the spine member;

wherein actuation of the trigger toward the handle causes the driving lever to pivot and bind against the spine member.

14. The apparatus of claim 13, wherein the actuation mechanism further includes:
   a braking lever operatively supported on the spine member, a first end of braking lever is pivotally positioned within a recess formed in the handle; and
   a spring member disposed between braking lever and a surface formed in the handle, wherein the spring member biases a free end of the braking lever in a distal direction.

15. The apparatus of claim 14, wherein the proximal end of the spine member extends from a proximal end of the handle.

16. The apparatus of claim 15, further comprising:
   an elongate dilation assembly operatively associatable with the yoke, the elongate dilation assembly including a handle, a radially expandable tubular sheath having a proximal end connected to the handle, a distal end, and defining an axial lumen with a first cross-sectional area.

17. The apparatus of claim 16, further comprising:
   an elongate expansion assembly operatively connectable to the at least one cuff, the expansion assembly including a tubular element having a distal end, a proximal end with a handle, and an axial lumen with a second cross-sectional area which is larger than the first cross-sectional area of the elongate dilation assembly.

18. A kit for providing access to a target surgical site, comprising:
   a radially expandable dilation assembly;
   a pneumoperitoneum needle assembly;
   a stylet;
   an expansion assembly;
   an obturator;
   an expansion assembly insertion apparatus for forming and enlarging a percutaneous penetration, the expansion assembly insertion apparatus including a first arm and a second arm, wherein the first arm is configured and dimensioned to selectively receive the dilation assembly to substantially inhibit axial movement of the dilation assembly relative to the first arm and the second arm is configured and dimensioned to selectively receive the expansion assembly to substantially inhibit axial movement of the expansion assembly relative to the second arm, wherein the first arm and the second arm are configured to maintain alignment between the dilation assembly and the expansion assembly; and
   a package for enclosing the radially expandable dilation assembly, the pneumoperitoneum needle assembly, the stylet, the expansion assembly, the obturator, and the expansion assembly insertion apparatus.

19. The kit according to claim 18, further comprising:
   a package insert including at least one of instructions on use and warnings of use.

20. The apparatus of claim 1, wherein the first engaging feature is U-shaped and includes a pair of proximal legs separated from a pair of distal legs to define a space therebetween.

21. The apparatus of claim 20, wherein the space defined between the pair of proximal legs and the pair of distal legs is configured and dimensioned to receive the handle of the dilation member.

22. The apparatus of claim 21, wherein the handle of the dilation member includes a pair of diametrically opposed tabs that are received within the space defined between the pair of proximal legs and the pair of distal legs such that the handle is releasably received by the first arm of the advancing apparatus.

* * * * *

UNITED STATES PATENT AND TRADEMARK OFFICE
CERTIFICATE OF CORRECTION

PATENT NO. : 7,479,150 B2  Page 1 of 1
APPLICATION NO. : 10/943132
DATED : January 20, 2009
INVENTOR(S) : Casba L. Rethy, Thomas Wenchell and Kourosh Azarbarzin

It is certified that error appears in the above-identified patent and that said Letters Patent is hereby corrected as shown below:

Title Page, Item (75) Inventors

The correct spelling of the second Inventor's name is: Thomas Wenchell

Signed and Sealed this

Tenth Day of March, 2009

JOHN DOLL
*Acting Director of the United States Patent and Trademark Office*